US009261566B2

(12) United States Patent
Gong et al.

(10) Patent No.: US 9,261,566 B2
(45) Date of Patent: Feb. 16, 2016

(54) DEVICE AND METHOD FOR IMPEDANCE ANALYSIS

(71) Applicant: INDUSTRIAL TECHNOLOGY RESEARCH INSTITUTE, Hsinchu (TW)

(72) Inventors: Cihun-Siyong Gong, Kaohsiung (TW); Yi-Feng Luo, Yilan County (TW); Li-Ren Huang, Zhubei (TW); Kai-Cheung Juang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 294 days.

(21) Appl. No.: 14/092,759

(22) Filed: Nov. 27, 2013

(65) Prior Publication Data

US 2015/0048853 A1 Feb. 19, 2015

(30) Foreign Application Priority Data

Aug. 16, 2013 (TW) .............................. 102129574 U

(51) Int. Cl.
G01R 31/36 (2006.01)
G01N 27/02 (2006.01)
A61B 5/053 (2006.01)
A61B 5/01 (2006.01)

(52) U.S. Cl.
CPC .............. *G01R 31/3634* (2013.01); *A61B 5/01* (2013.01); *A61B 5/053* (2013.01); *G01N 27/02* (2013.01)

(58) Field of Classification Search
CPC .......................... G01R 31/3634; G01N 27/02

USPC ................................................... 324/691–693
See application file for complete search history.

(56) References Cited

U.S. PATENT DOCUMENTS

| 6,653,817 | B2 | 11/2003 | Tate, Jr. et al. |
| 6,892,148 | B2 | 5/2005 | Barsoukov et al. |
| 7,197,487 | B2 | 3/2007 | Hansen et al. |
| 7,593,823 | B2 | 9/2009 | Iwane et al. |
| 7,619,390 | B2 | 11/2009 | Kim |

(Continued)

FOREIGN PATENT DOCUMENTS

| CN | 101827554 A | 9/2010 |
| TW | I320609 B | 2/2010 |

(Continued)

OTHER PUBLICATIONS

Robert M. Spotnitz, "AC Impedance Simulation for Lithium-Ion Cells", Battery Design Co. 2277 DeLucchi Drive, Pleasanton, CA 94588, www.batdesign.com, IEEE 2000 pages 121-126 .

(Continued)

*Primary Examiner* — Tung X Nguyen
*Assistant Examiner* — Robert P Alejnikov, Jr.
(74) *Attorney, Agent, or Firm* — Muncy, Geissler, Olds & Lowe, P.C.

(57) ABSTRACT

An impedance analysis device adapted to an object under test (OUT) includes a signal generator, a signal analysis unit and a processing unit. The signal generator outputs a pulse signal to the OUT. The signal analysis unit acquires a response signal which the OUT responds to the pulse signal, and analyzes the response signal to obtain an analysis parameter. The processing unit coupled to the signal analysis unit receives the analysis parameter, so as to obtain an impedance variation characteristic of the OUT.

17 Claims, 6 Drawing Sheets

(56) References Cited

U.S. PATENT DOCUMENTS

| | | | |
|---|---|---|---|
| 8,255,046 B2 | 8/2012 | Sarkar et al. | |
| 2002/0084771 A1* | 7/2002 | Lundberg | G01R 31/3648 320/134 |
| 2003/0071627 A1 | 4/2003 | Champlin | |
| 2005/0017685 A1 | 1/2005 | Rees et al. | |
| 2009/0226770 A1 | 9/2009 | Manabe et al. | |
| 2010/0121591 A1 | 5/2010 | Hall | |
| 2010/0213946 A1 | 8/2010 | Kirchev | |
| 2011/0018547 A1 | 1/2011 | Durston | |
| 2011/0077879 A1* | 3/2011 | Paryani | G01R 31/3662 702/63 |
| 2013/0179103 A1* | 7/2013 | Luo | G01R 31/3662 702/63 |

FOREIGN PATENT DOCUMENTS

| | | |
|---|---|---|
| TW | 201224485 A | 6/2012 |
| TW | 201329476 A1 | 7/2013 |
| TW | 201432274 A | 8/2014 |

OTHER PUBLICATIONS

Yevgen Barsukov, et al., "Battery Capacity Monitoring Accuracy and Implementation", 11 pages.

Keith James Keller, "Fine-tuning TI's Impedance Track™ battery fuel guage with LifePO$_4$ cells in shallow-discharge applications", Analog Applications Journal 1Q 2011 www.til.com/aaj, pp. 13-18.

B.S. Bhangu, et al., "Nonlinear Observers for Predicting State-of-Charge and State-of-Health of Lead-Acid Batteries for Hybrid-Electric Vehicles", IEEE Transactions on Vehicular Technology, vol. 54, No. 3, May 2005, pp. 783-794.

Michael Vega, "Single-Cell Impedance Track™ Gas Gauge for Novices", Texas Instruments Application Report SLUA422—Jun. 2007, 11 pages.

Martin Coleman, et al., "State-of-Charge Determination From EMF Voltage Estimation: Using Impedance, Terminal Voltage, and Current for Lead-Acid and Lithium-Ion Batteries", IEEE Transactions on Industrial Electronics, vol. 54, No. 5, Oct. 2007, pp. 2550-2557.

* cited by examiner

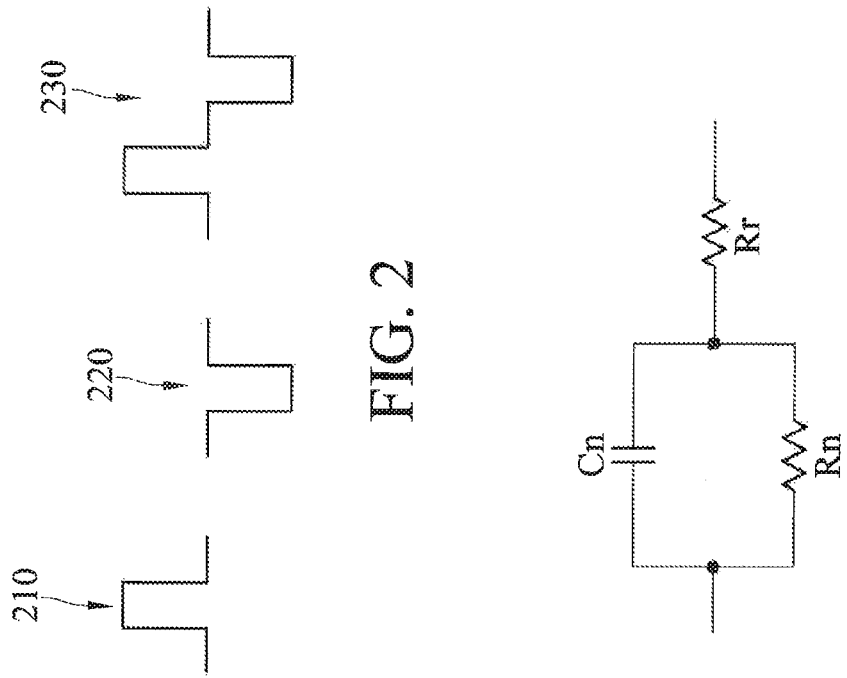
FIG. 2
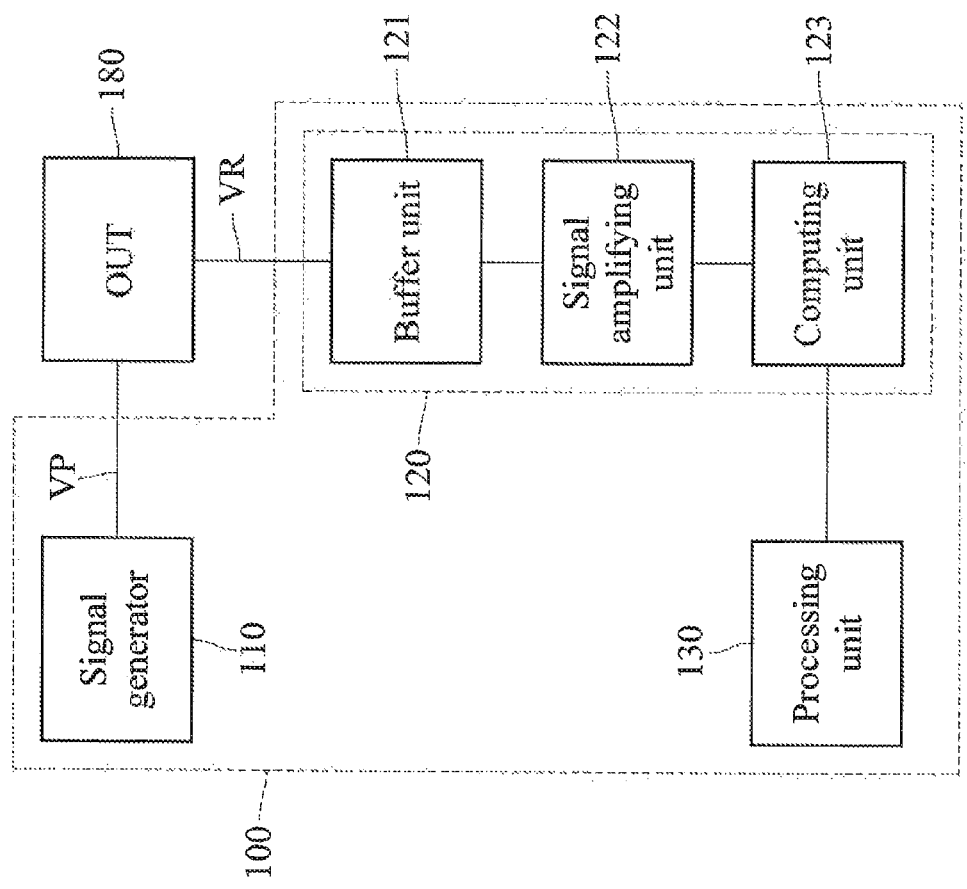
FIG. 3
FIG. 1

DEVICE AND METHOD FOR IMPEDANCE ANALYSIS

CROSS-REFERENCE TO RELATED APPLICATIONS

This non-provisional application claims priority under 35 U.S.C. §119(a) on Patent Application No(s). 102129574 filed in Taiwan, R.O.C. on 2013 Aug. 16, the entire contents of which are hereby incorporated by reference.

TECHNICAL FIELD

The disclosure relates to an impedance analysis technology. Particularly, the disclosure relates to an impedance analysis device and a method thereof.

BACKGROUND

The development of vehicle technology helps the interpersonal relationship and the living quality. Most vehicles use liquid fossil fuels such as gasoline, so it is not difficult to measure a quantity of the liquid fossil fuel used in such vehicles. But, people are becoming much more conscious and aware of the impact this has on the environment, so people are making more of an effort to reduce the dependence of petroleum. Thus, electric vehicles are much more advantaged because of their low environmental pollution, low noise, easy pollution control and various energy applications.

The electric vehicle is generally powered with a battery which is usually charged by a large current or discharges a large current, and it is not easy to accurately measure the remaining power capacity of battery. Thus, the management and analysis of battery is very important to the electric vehicle. Also, the state of charge (SOC) and state of health (SOH) of battery can be known by the variation of internal impedance and be estimated by the internal impedance variation and current temperature of a battery, where the SOC is the equivalent of a fuel gauge for the battery, and the SOH is a figure of merit of the current state of the battery, compared to its ideal conditions. Therefore, users can through the SOC, know when to charge the battery and through the SOH, know when to replace the battery.

Such an internal impedance measurement is performed by using an impedance track technology which mainly utilizes a DC impedance and an open-loop voltage to calculate an electrochemical capacity, and then looks up the SOC and SOH of battery in a look-up table according to the electrochemical capacity. However, the open-loop voltage is measured when the battery has a light load or is under a rest state, rather than when the battery is under an on-line state. Thus, the accuracy of looking up the SOC and SOH of battery in the look-up table may be poor.

Moreover, the result of battery information measurement is only updated at a specific time and can not be obtained in real time. In order to obtain the internal parameters of battery for deducing the SOC and SOH of battery in real time, it is necessary to supply an AC frequency conversion signal to the battery. Nevertheless, the AC frequency conversion signal may be make the circuit design more complicated, which leads to higher costs of production.

SUMMARY

An impedance analysis device according to an embodiment of the disclosure adapts to an object under test (OUT) and includes a signal generator, a signal analysis unit and a processing unit. The signal generator supplies a pulse signal to the OUT. The signal analysis unit acquires a response signal which the OUT responds to the pulse signal, and analyzes the response signal to obtain an analysis parameter. The processing unit is coupled to the signal analysis unit and receives the analysis parameter, so as to obtain an impedance variation characteristic of the OUT.

An impedance analysis method according to an embodiment of the disclosure adapts to an OUT and includes the following steps. A pulse signal is supplied to the OUT. A response signal which the OUT responds to the pulse signal is acquired and then is analyzed, so as to obtain an analysis parameter. According to the analysis parameter, an impedance variation characteristic of the OUT is obtained.

BRIEF DESCRIPTION OF THE DRAWINGS

The present disclosure will become more fully understood from the detailed description given herein below for illustration only and thus does not limit the present disclosure, wherein:

FIG. 1 is a schematic diagram of an impedance analysis device according to an embodiment of the disclosure;

FIG. 2 is a schematic diagram showing various embodiments of the pulse signal;

FIG. 3 is a schematic diagram of an equivalent circuit of the OUT;

DETAILED DESCRIPTION

Figure 4:
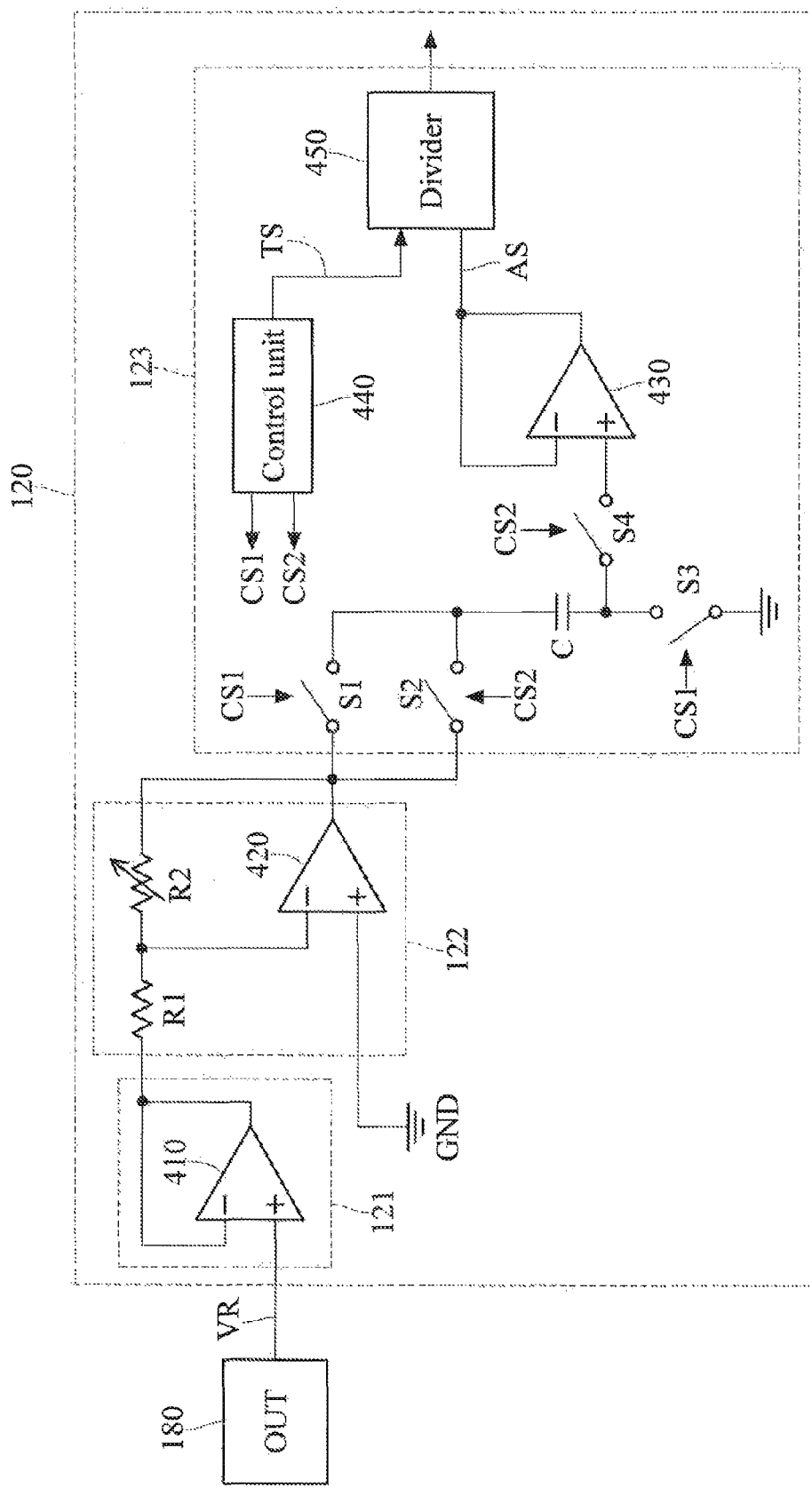
FIG. 4 is a schematic circuit diagram of the signal analysis unit.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing. Elements which are similar or equal to each other are identified with the same label in the disclosure.

FIG. 1 is a schematic diagram of an impedance analysis device according to an embodiment of the disclosure. An impedance analysis device 100 adapts to an OUT 180 which can be a battery module or a human body module or other similar OUTs in this and some embodiments. The impedance analysis device 100 includes a signal generator 110, a signal analysis unit 120 and a processing unit 130. The signal generator 110 and the signal analysis unit 120 are coupled to the OUT 180, and the processing unit 130 is coupled to the signal analysis unit 120.

The signal generator 110 supplies a pulse signal VP to the OUT 180. In this and some embodiments, the pulse signal VP is a positive pulse 210, a negative pulse 220 or a combination 230 of a positive pulse and a negative pulse as shown in FIG. 2, and its amplitude and width can be modulated.

The signal analysis unit 120 receives a response signal VR outputted by the OUT 180 when the OUT 180 responds to the pulse signal VP, and analyzes the response signal VR to obtain an analysis parameter. Specifically, the signal analysis unit 120 includes a buffer unit 121, a signal amplifying unit 122 and a computing unit 123. The buffer unit 121 couples to the signal amplifying unit 122, and the signal amplifying unit 122 couples to the computing unit 123. The buffer unit 121 receives the response signal VR to generate a buffer signal. The signal amplifying unit 122 receives the buffer signal from the buffer unit 121 and amplifies a gain of the response signal VR to generate an amplified signal. The computing unit 123 receives the amplified signal from the signal amplifying unit 122 and analyzes the response signal VR to generate the analysis parameter according to the amplified signal and a time difference signal. For instance, the computing unit 123 performs a slope analysis procedure on the response signal VR to generate the analysis parameter specifying a slope.

The processing unit 130 receives the analysis parameter outputted by the computing unit 123, to obtain the impedance variation characteristic of the OUT 180. An equivalent model of the OUT 180 is shown in FIG. 3. A resistor Rr is a real part of the impedance of the OUT 180, and a capacitor Cu and a resistor Rn, which are connected to each other in parallel, indicate an imaginary part of the impedance of the OUT 180 and specify the frequency of the OUT 180. Alternately, the equivalent circuit of the OUT 180 can be any circuit including a real part of the impedance, e.g. resistors, and an imaginary part of the impedance, e.g. any possible combination of resistors, inductors and capacitors.

Through the above analysis procedure, the disclosure may obtain more internal parameter characteristics of the OUT 180 which are more accurate, thereby analyzing the characteristics of the OUT 180 more accurately. As the following, there are two exemplary embodiments of OUT 180 taken to illustrate the characteristic analysis.

Take a battery module as an example of the OUT 180. After obtaining the impedance variation characteristic of the battery module, the processing unit 130 analyzes a relation between the electrochemical variation and impedance variation of the battery module according to the impedance variation characteristic and a temperature signal of the battery module, so as to estimate the SOC and SOH of the battery module or the physical characteristics of the battery module. The temperature signal hereinafter is a current ambient temperature of the battery module during the analysis. The impedance variation characteristic of the battery module is equivalent to the internal electrochemical variation caused by the various usage periods or usage time of the battery module, and the electrochemical variation represents the impedance variation at the frequency domain and represents voltage signal having various slopes at the time domain. In this way, without any battery database, the disclosure can still accurately estimate the SOC and SOH of the battery module or the physical characteristics of the battery module and then reports the estimation result to the back-end system, so that users can know the current state of the battery module and know when to swap the battery module.

Alternately, take a human body module as an example of the OUT 180, where the human body module is formed by integrating an electrode-body contact interface (EBCI) with the human skin. The signal generator 110 supplies the pulse signal VP to the human skin through the EBCI, and then the human skin responds the response signal VR to the pulse signal VP and sends the response signal VR to the signal analysis unit 120 through the EBCI. After obtaining the impedance variation characteristic of the human body module, the processing unit 130 can estimate the interface state and SOH or physical characteristics of the human body module according to the impedance variation characteristic and temperature signal of the human body module. The temperature signal hereinafter is a current ambient temperature of the human body module during the analysis. The impedance variation characteristic of the human body module is basically the electrochemical effect, i.e. the oxidation-reduction reaction, at the interface between the human skin and the electrode which has been used for a long time period, and represents the impedance variation at the frequency domain and the voltage signal having various slopes at the time domain. In this way, without any human body module database, the disclosure can accurately estimate the interface state and SOH or physical characteristics of the human body module and then reports the estimation result to the back-end system. Thus, users can know their health state or other people's health state or the usage state of the EBCI.

Moreover, the impedance analysis device 100 can analysis the OUT 180 on line and report the current states of the OUT 180 in real time. The current states of the OUT 180 can be the interface state and SOH or physical characteristics of the human body module or be the SOC and SOH or physical characteristics of the battery module. Also, the impedance analysis device 100 in this and some embodiments can be embodied in an integrated circuit (IC) chip which can be applied to the human body module or a device, e.g. a smart phone, a tablet computer, a notebook or a vehicle, having a battery module, in order to efficiently and accurately estimate the impedance variation characteristic of the OUT 180, e.g. the human body module or the battery module, in real time. Thus, users can know about the current states of the OUT 180 in real time, so as to deal with the OUT 180 in suitable time.

FIG. 4 is a schematic diagram of the signal analysis unit. The buffer unit 121 includes a first operation amplifier 410 which has a first input end, i.e. a positive input end, a second input end, i.e. a negative input end, an output end, and the second input end and output end of the first operation amplifier 410 are coupled to each other. The first input end of the first operation amplifier 410 receives the response signal VR from the OUT 180, and then the output end of the first operation amplifier 410 outputs the buffer signal.

The signal amplifying unit 122 includes a first resistor R1, a second operation amplifier 420 and a second resistor R2. The first resistor R1 has a first end and a second end, and the first end of the first resistor R1 receives the buffer signal from the output end of the first operation amplifier 410. The second operation amplifier 420 has a first input end, i.e. a positive input end, a second input end, i.e. a negative input end, and an output end. The first input end of the second operation amplifier 420 is grounded, the second input end of the second operation amplifier 420 couples to the second end of the first resistor R1, and the output end of the second operation amplifier 420 outputs the amplified signal. The second resistor R2 has a first end and a second end. The first end of the second resistor R2 couples to the second end of the second operation amplifier 420, and the second end of the second resistor R2 couples to the output end of the second operation amplifier 420. The second resistor R2 in this and some embodiments can be an adjustable resistor, so that users can adjusts the resistance value of the second resistor R2 to change an amplifying power for the amplified signal outputted by the second operation amplifier 420.

The computing unit 123 includes a first switch S1, a second switch S2, a capacitor C, a third switch S3, a fourth switch S4, a subtracter 430, a control unit 440 and a divider 450. The first switch S1 has a first end, a second end and a control end. The first end of the first switch S1 receives the buffer signal, and the control end of the first switch S1 is controlled with a first control signal CS1, so as to control the second end of the first switch to output the buffer signal. The second switch S2 has a first end, a second end and a control end. The first end of the second switch S2 couples to the first end of the first switch S1, and the control end of the second switch S2 is controlled with a second control signal CS2, so as to control the second end of the second switch S2 to output the buffer signal. The capacitor C has a first end and a second end. The first end of the capacitor C couples to the second end of the first switch S1 and the second end of the second switch S2. The third switch S3 has a first end, a second end and a control end. The first end of the third switch S3 couples to the second end of the capacitor C, the second end of the third switch S3 is grounded, and the control end of the third switch S3 is controlled with the first control signal CS1, so as to control the first end of the third switch S3 to couple to the second end of the third switch The fourth switch S4 has a first end, a second end and a control end. The first end of the fourth switch S4 couples to the second end of the capacitor C, and the control end of the fourth switch S4 is controlled with the first control signal CS1, so as to control the first end of the fourth switch S4 to couple to the second end of the fourth switch S4.

The subtracter 430 has a first input end, a second input end and an output end. The first input end of the subtracter 430 couples to the second end of the fourth switch S4, and the output end of the subtracter 430 couples to the second input end of the subtracter 430 and outputs the computing signal AS. The control unit 440 generates a first control signal CS1 in the first time period, and generates a second control signal CS2 in the second time period, and outputs a time difference signal TS associated with a difference between the first time period and the second time period. The first time period precedes the second time period.

The divider 450 couples to the output end of the control unit 440 and the output end of the subtracter 430, receives the computing signal AS and the time difference signal TS, and performs division on the computing signal AS and the time difference signal TS to generate the analysis parameter. For instance, the analysis parameter is obtained by dividing the computing signal AS with the time difference signal TS.

Accordingly, the detailed operation to obtain the impedance variation characteristic of the OUT 180 is described as follows. Firstly, when the signal generator 110 supplies the pulse signal VP to the OUT 180, the OUT 180 responds the response signal VR to the pulse signal VP and then sends the response signal VR to the buffer unit 121, i.e. the first input end of the first operation amplifier 410, where the first operation amplifier 410 can isolate the response signal VR from being interfered by the back-end circuits.

Subsequently, the slope analysis procedure is performed as follows. The buffer unit 121 buffers the response signal VR to generate a buffer signal and sends the buffer signal to the signal amplifying unit 122, i.e. the first end of the first resistor R1. The signal amplifying unit 122 scales the buffer signal up to generate the amplified signal according to a resistance ratio of the first resistor R1 to the second resistor R2, and sends the amplified signal to the computing unit 123. Herein, the control unit 440 in the first time period (t1) outputs the first control signal CS1 at a high logic level to the first switch S1 and the third switch S3, so as to turn on the first switch S1 and the third switch S3. Then, the amplified signal charges the capacitor C, so that a first voltage (V1) between the two ends of the capacitor C will be applied to the first input end of the subtracter 430. The voltage potential at the output end of the subtracter 430 will be the first voltage (V1).

In the second time period (t2), the control unit 440 outputs the second control signal CS2 at a high logic level to the second switch S2 and the fourth switch S4, and the first control signal CS1 at a low logic level to the first switch S1 and the third switch S3, so as to turn on the second switch S2 and the fourth switch S4 and turn off the first switch S1 and the third switch S3. Herein, the voltage difference between the two ends of the capacitor C is still the first voltage (V1), so the voltage potential at the second end of the capacitor C will be the second voltage (V2) which is the first voltage plus the voltage potential of the response signal VR. Then, the second voltage (V2) will be applied to the first input end of the subtracter 430. As a result, the subtracter 430 further performs subtraction on the first voltage (V1) at its second input end and the second voltage (V2) at its first input end to obtain the computing signal AS. For example, the subtracter 430 subtracts the first voltage V1 from the second voltage V2 to obtain the computing signal AS. That is, the voltage potential of the computing signal AS is the second voltage V2 minus the first voltage V1.

Moreover, the control unit 440 outputs the time difference signal TS specifying a difference between the first time period (t1) and the second time period (t2), to the divider 450. After receiving the computing signal AS and the time difference signal TS, the divider 450 performs division on the computing signal AS and the time difference signal TS to generate the analysis parameter, i.e. (V2−V1)/(t2−t1), specifying a slope, and then sends the analysis parameter to the processing unit 130. Accordingly, the processing unit 130 can obtain the impedance variation characteristic of the OUT 180 according to the analysis parameter.

Figure 5:
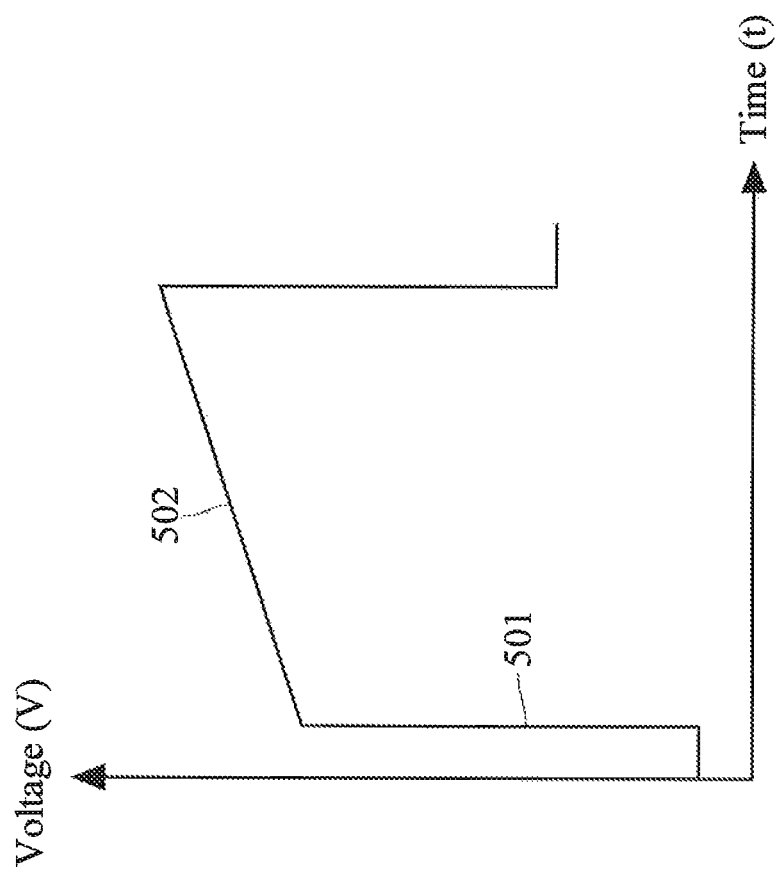
FIG. 5 is a simulative waveform diagram of the OUT in FIG. 3.

An experimental simulation to the OUT 180 is taken as shown in FIG. 5. The label 501 represents the amplitude of the pulse signal VR and corresponds to the resistor Rr associated with the real part of the equivalent model, and the label 502 represents the analysis parameter specifying a slope and corresponds to the resistor Rn and the capacitor Cn which connect to each other in parallel and are associated with the imaginary part of the equivalent model. Thus, the processing unit 130 can obtain the impedance variation characteristic of the OUT 180 according to the analysis parameter and the amplitude of the pulse signal VP.

According to the above description, the operation of the impedance analysis device 100 in FIG. 1 can be summarized in various embodiments of an impedance analysis method which are described below.

Figure 6:
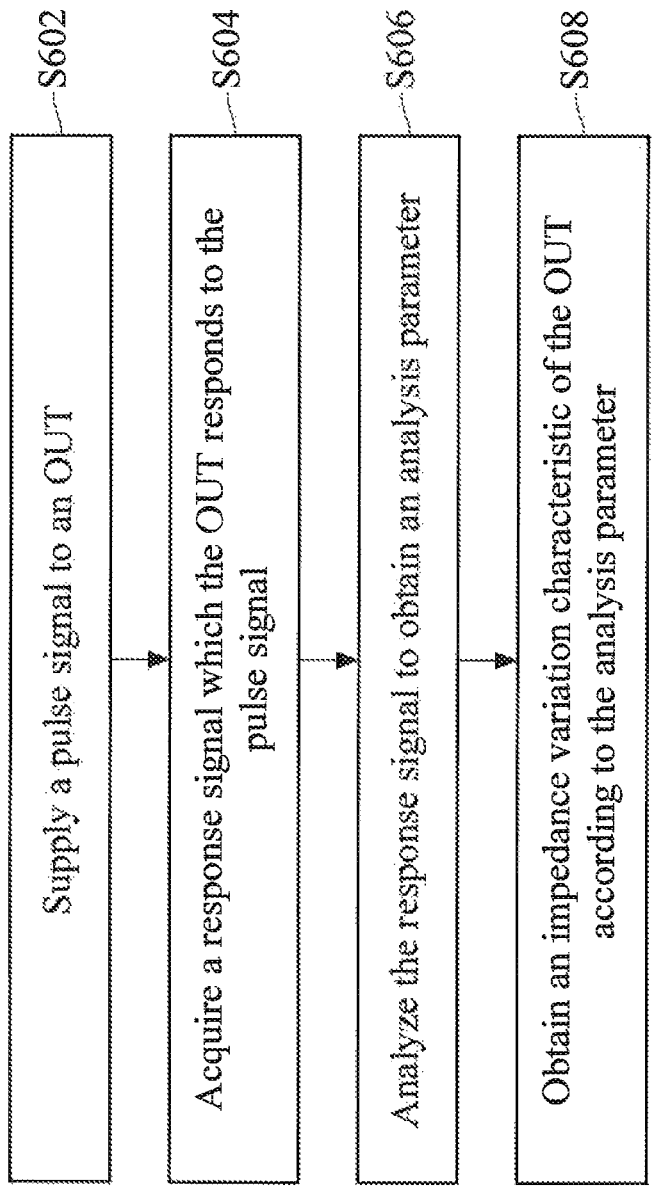
FIG. 6 is a flowchart of an impedance analysis method according to an embodiment of the disclosure.

FIG. 6 is a flowchart of an impedance analysis method according to an embodiment of the disclosure. The impedance analysis method is adapted to an OUT. Firstly, a pulse signal is supplied to the OUT in step S602. Then, a response signal which the OUT responds to the pulse signal is acquired in step S604, and is analyzed in step S606, so as to generate an analysis parameter. According to the analysis parameter, an impedance variation characteristic of the OUT can be obtained in step S608.

Figure 7:
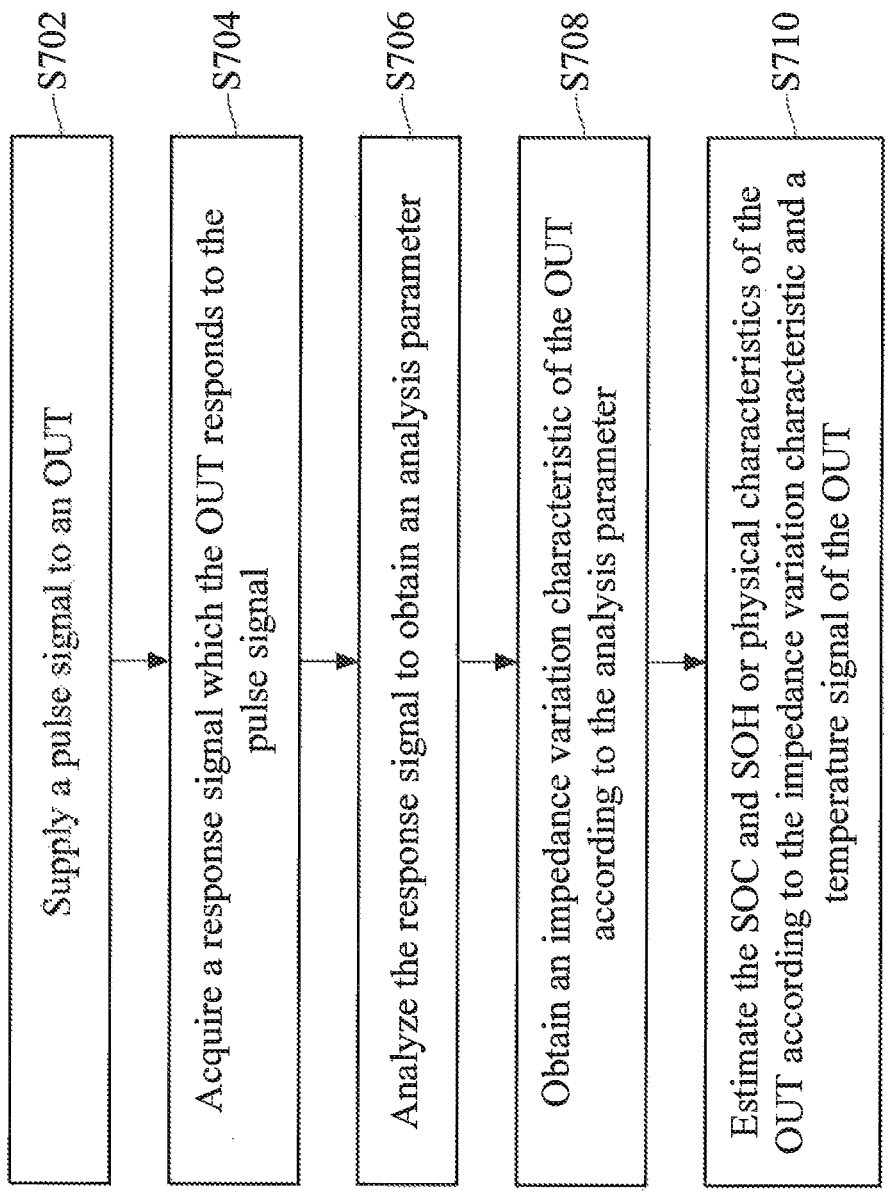
FIG. 7 is a flowchart of an impedance analysis method according to an embodiment of the disclosure.

FIG. 7 is a flowchart of an impedance analysis method according to an embodiment of the disclosure. In this embodiment, a battery module is taken as an example of the OUT. Firstly, a pulse signal is supplied to the OUT in step S702. Then, a response signal which the OUT responds to the pulse signal is acquired in step S704, and is analyzed in step S706, so as to generate an analysis parameter. According to the analysis parameter, an impedance variation characteristic of the OUT can be obtained in step S708, and according to the impedance variation characteristic and a temperature signal of the OUT, the SOC and SOH of the OUT or the physical characteristics of the OUT can be estimated in step S710.

Figure 8:
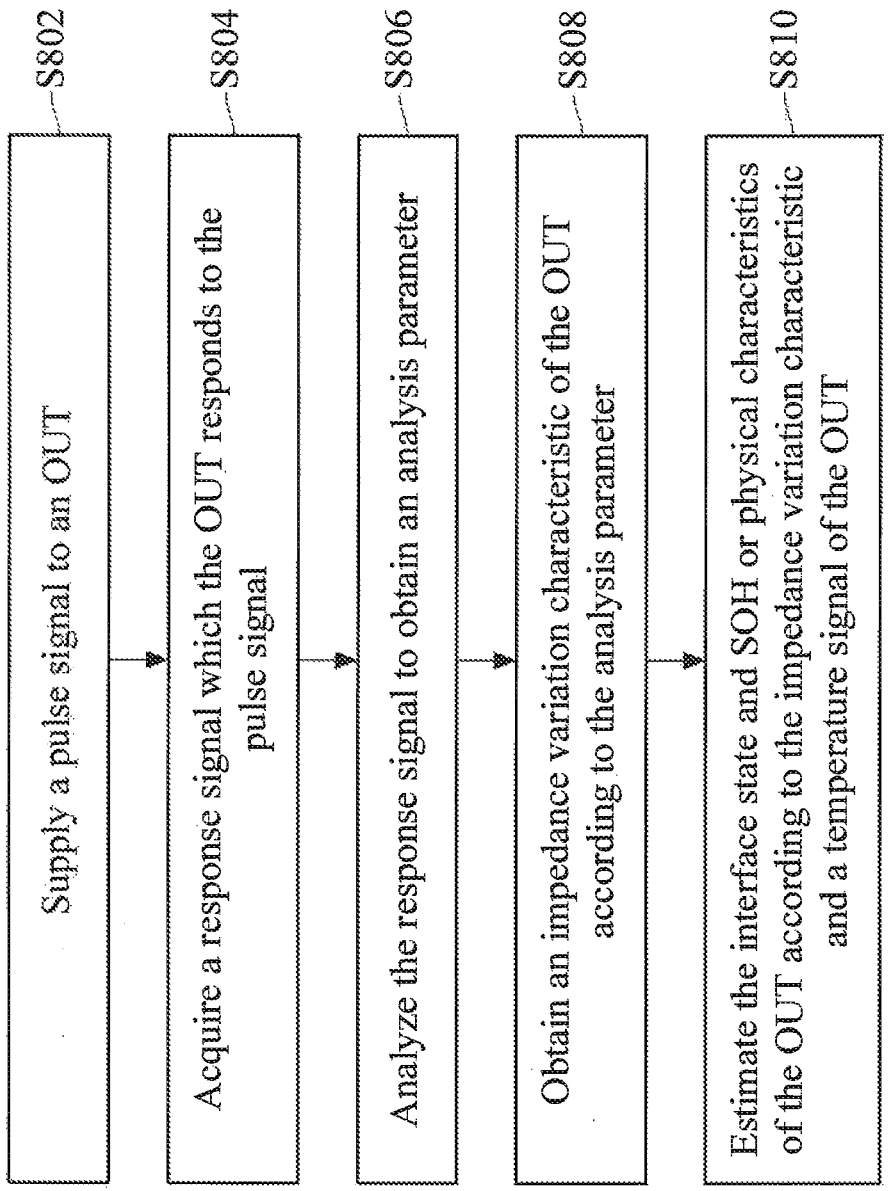
FIG. 8 is a flowchart of an impedance analysis method according to an embodiment of the disclosure.

FIG. 8 is a flowchart of an impedance analysis method according to an embodiment of the disclosure. In this embodiment, a human body module is taken as an example of the OUT. Firstly, a pulse signal is supplied to the OUT in step S802. Then, a response signal that the OUT responds to the pulse signal is acquired in step S804, and is analyzed in step S806, so as to generate an analysis parameter. According to the analysis parameter, an impedance variation characteristic of the OUT can be obtained in step S808, and according to the impedance variation characteristic and a temperature signal of the OUT, the interface state and SOH of the OUT or the physical characteristics of the OUT can be estimated in step S810.

In the above embodiments, the pulse signal can be a positive pulse, a negative pulse or a combination of a positive pulse and a negative pulse, and its amplitude and width can be modulated. Moreover, the impedance analysis method can be performed on line in real time, so as to in real time report the current states of the OUT which can be the interface state and SOH or physical characteristics of the human body module or be the SOC and SOH or physical characteristics of the battery module. Accordingly, the analysis of the OUT can be speeded up and becomes more efficient.

As set forth above, the disclosure supplies the pulse signal to the OUT to acquire the response signal which the OUT responds to the pulse signal, and then the disclosure further analyzes the response signal to obtain the analysis parameter through which the disclosure can obtain the impedance variation characteristic of the OUT. Subsequently, the current usage states of the OUT in various aspects can be estimated more accurately according to the impedance variation characteristic and current temperature of the OUT on line without any relative database and be reported to users in real time. Thus, the users can deal with the OUT at suitable time, and the analysis of the OUT can be speeded up as well.

If the OUT is a battery module, the users can know about the current states of the battery module such as the SOC and SOH or the physical characteristics in real time when the battery module is under a light load state or under a rest state. If the OUT is a human body module, the users can know about the current states of the human body module such as the interface state and SOH or the physical characteristics, or about the current states of someone else in real time.

What is claimed is:

1. An impedance analysis device, adapted to on object under test (OUT) and comprising:
    a signal generator, configured to supply a pulse signal to the OUT;
    a signal analysis unit, configured to acquire a response signal which the OUT responds to the pulse signal, and then analyze the response signal to obtain an analysis parameter; and
    a processing unit, coupled to the signal analysis unit and configured to receive the analysis parameter from the signal analysis unit, so as to obtain an impedance variation characteristic of the OUT; and
    wherein the signal analysis unit comprises: a buffer unit, configured to receive the response signal to output a buffer signal;
    a signal amplifying unit, coupled to the buffer unit and configured to amplify a gain of the buffer signal to output an amplified signal;
    a computing unit, coupled to the signal amplifying unit and configured to receive the amplified signal, and according to the amplified signal and a time difference signal, analyze the response signal to output the analysis parameter; and
    wherein the computing unit comprises:
    a first switch having a first end, a second end and a control end, the first end of the first switch receiving the buffer signal, and the control end of the first switch being controlled with a first control signal, so as to control the second end of the first switch to output the buffer signal;
    a second switch having a first end, a second end and a control end, the first end of the second switch being coupled to the first end of the first switch, and the control end of the second switch being controlled with a second control signal, so as to control the second end of the second switch to output the buffer signal;
    a capacitor having a first end and a second end, and the first end of the capacitor being coupled to the second end of the first switch and the second end of the second switch;
    a third switch having a first end, a second end and a control end, the first end of the third switch being coupled to the second end of the capacitor, the second end of the third switch being grounded, and the control end of the third switch being controlled with the first control signal, so as to couple the first end of the third switch to the second end of the third switch;
    a fourth switch having a first end, a second end and a control end, the first end of the fourth switch being coupled to the second end of the capacitor, and the control end of the fourth switch being controlled with the first control signal, so as to couple the first end of the fourth switch to the second end of the fourth switch;
    a subtracter having a first input end, a second input end and an output end, the first input end of the subtracter being coupled to the second end of the fourth switch, the output end of the subtracter being coupled to the second input end of the subtracter for outputting a computing signal;
    a control unit configured to output the first control signal in a first time period, to output the second control signal in a second time period, and to output the time difference signal associated with a difference between the first time period and the second time period, and the first time period preceding the second time period; and
    a divider coupled to the control unit and the output end of the subtracter and configured to receive the computing signal and the time difference signal and perform division on the computing signal and the time difference signal to generate the analysis parameter.

2. The impedance analysis device according to claim 1, wherein the buffer unit comprises:
    a first operation amplifier having a first input end, a second input end and an output end, the first input end of the first operation amplifier receiving the response signal, the second input end of the first operation amplifier coupled to the output end of the first operation amplifier for outputting the buffer signal.

3. The impedance analysis device according to claim 1, wherein the signal amplifying unit comprises:
    a first resistor having a first end and a second end, the first end of the first resistor receiving the buffer signal;
    a second operation amplifier having a first input end, a second input end and an output end, the first input end of the second operation amplifier being grounded, the second input end of the second operation amplifier being coupled to the second end of the first resistor, and the output end of the second operation amplifier outputting the amplified signal; and
    a second resistor having a first end and a second end, the first end of the second resistor being coupled to the second end of the second operation amplifier, and the second end of the second resistor being coupled to the output end of the second operation amplifier.

4. The impedance analysis device according to claim 1, wherein the pulse signal is a positive pulse, a negative pulse or a positive pulse plus a negative pulse.

5. The impedance analysis device according to claim 1, wherein amplitude and width of the pulse signal are flexible.

6. The impedance analysis device according to claim 1, wherein the OUT is a battery module, the processing unit further estimates state of charge (SOC) and state of health (SOH) of the OUT or physical characteristics of the OUT according to the impedance variation characteristic and a temperature signal of the OUT.

7. The impedance analysis device according to claim 1, wherein the OUT is a human body module, the processing unit further estimates interface state and SOH of the OUT or physical characteristics of the OUT according to the impedance variation characteristic and a temperature signal of the OUT.

8. The impedance analysis device according to claim 1, wherein the impedance analysis device analyzes the OUT on line in real time.

9. The impedance analysis device according to claim 1, wherein the impedance analysis device is integrated into a chip which is disposed on a human body module or a device having a battery.

10. The impedance analysis device according to claim 1, wherein the signal analysis unit performs a slope analysis procedure to obtain the analysis parameter specifying a slope.

11. An impedance analysis method, adapted to an OUT and comprising:
providing a signal generator, configured to supply a pulse signal to the OUT;
providing a signal analysis unit, configured to acquire a response signal which the OUT responds to the pulse signal, and then analyze the response signal to obtain an analysis parameter; and
providing a processing unit, coupled to the signal analysis unit and configured to receive the analysis parameter from the signal analysis unit, so as to obtain an impedance variation characteristic of the OUT; and
wherein the signal analysis unit comprises: a buffer unit, configured to receive the response signal to output a buffer signal;
a signal amplifying unit, coupled to the buffer unit and configured to amplify a gain of the buffer signal to output an amplified signal;
a computing unit, coupled to the signal amplifying unit and configured to receive the amplified signal, and according to the amplified signal and a time difference signal, analyze the response signal to output the analysis parameter; and
wherein the computing unit comprises:
a first switch having a first end, a second end and a control end, the first end of the first switch receiving the buffer signal, and the control end of the first switch being controlled with a first control signal, so as to control the second end of the first switch to output the buffer signal;
a second switch having a first end, a second end and a control end, the first end of the second switch being coupled to the first end of the first switch, and the control end of the second switch being controlled with a second control signal, so as to control the second end of the second switch to output the buffer signal;
a capacitor having a first end and a second end, and the first end of the capacitor being coupled to the second end of the first switch and the second end of the second switch;
a third switch having a first end, a second end and a control end, the first end of the third switch being coupled to the second end of the capacitor, the second end of the third switch being grounded, and the control end of the third switch being controlled with the first control signal, so as to couple the first end of the third switch to the second end of the third switch;
a fourth switch having a first end, a second end and a control end, the first end of the fourth switch being coupled to the second end of the capacitor, and the control end of the fourth switch being controlled with the first control signal, so as to couple the first end of the fourth switch to the second end of the fourth switch;
a subtracter having a first input end, a second input end and an output end, the first input end of the subtracter being coupled to the second end of the fourth switch, the output end of the subtracter being coupled to the second input end of the subtracter for outputting a computing signal;
a control unit configured to output the first control signal in a first time period, to output the second control signal in a second time period, and to output the time difference signal associated with a difference between the first time period and the second time period, and the first time period preceding the second time period; and
a divider coupled to the control unit and the output end of the subtracter and configured to receive the computing signal and the time difference signal and perform division on the computing signal and the time difference signal to generate the analysis parameter;
supplying a pulse signal to the OUT; acquiring a response signal which the OUT responds to the pulse signal;
analyzing the response signal to obtain an analysis parameter; and
obtaining an impedance variation characteristic of the OUT according to the analysis parameter.

12. The impedance analysis method according to claim 11, wherein the pulse signal is a positive pulse, a negative pulse or a positive pulse plus a negative pulse.

13. The impedance analysis method according to claim 11, wherein amplitude and width of the pulse signal are flexible.

14. The impedance analysis method according to claim 11, wherein the OUT is a battery module, and the impedance analysis method further comprises:
estimating SOC and SOH of the OUT or physical characteristics of the OUT according to the impedance variation characteristic and a temperature signal of the OUT.

15. The impedance analysis method according to claim 11, wherein the OUT is a human body module, the impedance analysis method further comprises:
estimating interface state and SOH of the OUT or physical characteristics of the OUT according to the impedance variation characteristic and a temperature signal of the OUT.

16. The impedance analysis method according to claim 11, wherein the OUT is analyzed on line in real time.

17. The impedance analysis method according to claim 11, wherein a slope analysis procedure is performed to obtain the analysis parameter specifying a slope.

* * * * *